United States Patent [19]

Thompson

[11] Patent Number: 4,963,416
[45] Date of Patent: Oct. 16, 1990

[54] METHOD TO REDUCE THE DAMAGE CAUSED BY IONIZING RADIATION TO POLYURETHANE/POROUS EXPANDED POLYTETRAFLUROETHYLENE COMPOSITES BY USE OF HINDERED PHENOLS

[75] Inventor: Robert M. Thompson, Wilmington, Del.

[73] Assignee: W. L. Gore & Associates, Inc., Newark, Del.

[21] Appl. No.: 435,642

[22] Filed: Nov. 13, 1989

[51] Int. Cl.$^5$ .................. B32B 27/08; B32B 27/40
[52] U.S. Cl. ................... 428/315.5; 428/315.7; 428/422; 428/424.6; 524/739
[58] Field of Search ............. 428/306.6, 315.5, 315.7, 428/315.9, 422, 424.6; 524/739

[56] References Cited

U.S. PATENT DOCUMENTS

| | | |
|---|---|---|
| 4,443,511 | 4/1984 | Worden ............................. 428/422 |
| 4,539,255 | 9/1985 | Sato et al. ....................... 428/315.5 |
| 4,636,424 | 1/1987 | Amemiya et al. ................ 428/315.5 |
| 4,692,369 | 9/1987 | Nomi ................................. 428/422 |
| 4,814,412 | 3/1989 | Crowther et al. ............... 428/306.6 |

OTHER PUBLICATIONS

Modern Plastics Encyclopedia, 1985–1986, p. 578.

Primary Examiner—William J. Van Balen
Attorney, Agent, or Firm—Gary A. Samuels

[57] ABSTRACT

Polyurethane/expanded porous polytetrafluoroethylene composite coatings show unexpectedly high resistance to ionizing radiation when they contain a hindered phenol.

3 Claims, No Drawings

METHOD TO REDUCE THE DAMAGE CAUSED BY IONIZING RADIATION TO POLYURETHANE/POROUS EXPANDED POLYTETRAFLUROETHYLENE COMPOSITES BY USE OF HINDERED PHENOLS

FIELD OF THE INVENTION

This invention relates to a method of stabilizing coated fabrics to ionizing radiation.

More particularly, the invention relates to a method of stabilizing composite coatings of porous expanded polytetrafluoroethylene and breathable polyurethanes for use in surgical drapes and gowns to ionizing radiation used to sterilize said surgical drapes and gowns by use of hindered phenols.

BACKGROUND OF THE INVENTION

Surgical gowns and drapes protect surgically prepared areas of the skin from contamination and also protect surgeons and nurses against contamination through contact with unprepared or contaminated areas of patient's skin. Preferably, surgical gowns should also present a sterile barrier to protect patients from contamination through contact with the surgeon, and vice versa.

Body liquids and other liquids can permeate through ordinary liquid resistant surgical gowns or drapes. Thus, bacteria, viruses, and bloodborne pathogens which may be present on one surface of the gown or drape may be transported through the gown to the patient or the operating room personnel. Thus, liquid imperviousness of the gown or drape is recognized as an important property.

It has been widely recognized that the gowns and drapes should be "breathable" to be comfortable, i.e., allow water vapor to pass through. It is not necessary that air pass through, only that water vapor from perspiration be transmitted from inside to outside so that undergarments do not become wet and so that a natural evaporative cooling effect can be achieved. Breathability and ability to transport interior moisture vapor to the external environment are used interchangeably herein, If a continuous film of hydrophilic material is exposed to air containing substantial water vapor on one side of the film, and to air containing less water vapor on the other side, the side of the film exposed to the higher water vapor concentration will absorb water molecules which diffuse through the film and are desorbed or evaporated on the side exposed to the lower water vapor concentration. Thus, water vapor is effectively transported through the film on a molecule by molecule basis. This property is known as "breathability".

Liquid water impermeability can be achieved in materials for use in surgical drapes and gowns by use of various impervious films such as polyethylene or plasticized PVC laminated to a fabric. Such fabrics are, however, not breathable and can be very uncomfortable to wear.

Both breathability and liquid water impermeability can be achieved readily with composite coatings of expanded porous polytetrafluoroethylene and hydrophilic polyurethanes. These coatings can then be attached to one or more layers of cloth to provide laminates which have all of the aforementioned properties desireable in surgical drapes and gowns.

However, the current trend of sterilizing operating room (O.R.) equipment, including surgical drapes and gowns, with ionizing radiation has thwarted efforts to use these polyurethane/expanded porous polytetrafluoroethylene composites because of degradation of the composite caused by the radiation. The radiation causes the composite to become gummy and to discolor.

This degradation of the composite is unexpected because generally polyurethanes are known to be resistant to degradation from ionizing or gamma radiation, as seen by Lawandy and Hepburn, Elastomerics 21-24, January 1981; and Klimanova, et al., Soviet Plastics No. 3, 23-25 (1973). Polymers in the former article, although showing signs of change, were still intact after 20 M. rads of cobalt 60 source gamma irradiation. In the latter article, exposures up to 200 M.rads are described and in several cases, the tensile strength was still higher after 200 M.rads dosage over the tensile strength unexposed samples. Polyurethane acrylates (Tu, SME Assoc. for Finish Processes, Sept. 1980 Conference, P. 117-143) sometimes develop color with either U.V. light or electron beam energy, and it has been reported that hindered phenols are effective in retarding color development.

In contrast to the stability of polyurethanes on exposure to ionizing radiation, expanded porous polytetrafluoroethylene is extremely sensitive to ionizing radiation, losing tensile strength even at less than one M.rad exposure in air. Thus, the composite, being made of a radiation stable polyurethane and a radiation unstable polytetrafluoroethylene would be expected to be better in stability than the polytetrafluoroethylene alone. However, the composite of polyuiethane and expanded porous polytetrafluoroethylene shows sensitivity to ionizing radiation similar to the sensitivity of the expanded porous polytetrafluoroethylene alone. That was unexpected because other properties of such coating composites resemble these of the polyurethane more than those of the expanded porous polytetrafluoroethylene.

It is mitigation of this sensitivity of such expanded porous polytetrafluoroethylene-polyurethane composites to ionizing radiation that this invention is directed.

SUMMARY OF THE INVENTION

This invention comprises reducing sensitivity of ionizing radiation to polyurethane-expanded polytetrafluoroethylene composites by adding a hindered phenol to the composite.

DESCRIPTION OF THE INVENTION

In the course of development of coated fabrics, particularly as viral barriers, the use of a thin scaffold of expanded porous polytetrafluoroethylene (EPTFE) filled with a breathable polyurethane and attached to woven or knitted fabric was found to be beneficial. However, the ionizing radiation used to sterilize these coated fabrics for use in operating rooms, was not expected to decompose the breathable polyurethane portion of the composite as much as it did. In fact, as seen in Table 1, the effect of even 5 M.rad of gamma radiation completely destroyed the EPTFE when tested alone, but polyurethane films alone were even stronger than before irradiation. However, the composite, consisting of the EPTFE and polyurethane lost 68% of its tensile strength after 2.5 M. rad and 70% after 5.0 M. rad treatment. This great loss seems to be due, it is hypotherized, to free radicals being formed in the EPTE which attack the polyurethane.

Loss of tensile strength in polyurethanes resulting from low dosages of ionizing radiation appears to be unique to polyurethane/EPTFE composites. Apparently the presence of EPTFE results in a synergistic decomposition of the composite.

Hindered phenols, such as Irganox®1010 (tetrakis [methylene (3,5-di-tert-butyl-4-hydroxyhydrocinnamate)] methane and Irganox 1035 (thiodiethylene bis(3,5-di-tert-butyl-4-hydroxyhydrocinnamate), both available from Ciba-Geigy Corp., even at concentrations as low as 1%, effectively reduce radiation damage to the polyurethane-EPTFE composite. It is hypothesized that the EPTFE is being used up, and that the hindered phenol protect the polyurethane from the destructive effect of by products of the EPTFE decomposition, so that up to 80% of the composite's tensile strength is retained after 2.5 M. rad and up to 66% after 5 M. rad dosages. It is expected that other hindered phenols will work similarly in the protection of polyurethane-EPTFE composites from massive destruction by ionizing high energy radiation.

EXAMPLES

Preparation of Polyurethane Resins

A 1000 ml. resin kettle was purged with dry nitrogen and 104 g. (0.832 molar equivalents) of 4,4'- diphenymethane diisocyanate was added. The temperature was raised to 60° C. to melt the isocyanate and 286 g. (0.415 molar equivalents) of polyethylene glycol 1400 (previously dried to less than 200 ppm. water) was added. The temperature was increased to 100°–101° C. and the reaction mass was stirred for about 1½ hours when the NCO content was about 4.4% by titration.

If a hindered phenol was to be added, it was at this stage of the reaction. One percent of phenol (4.0 g. each of either Irganox 1010 or Irganox 1035 products of Ciba-Geigy Corp. was used). The temperature is increased to 106°–107° C. and 10.4 g. (0.10 eq.) of 4,4'-hydroquinone bis (2-hydroxyethyl) ether was added. The whole was stirred until the NCO content reached 3% in about 1½ hours. The liquid mass was discharged into pint cans and sealed under nitrogen.

Coated Membranes

Coatings were prepared using expanded porous polytetrafluoroethylene membrane, weight 2.5 g./yd.$^2$, and the hydrophilic polyurethane prepolymer described in the above example. The prepolymer was applied to the membrane by means of a transfer roll to yield 14 g./yd.$^2$ coatings (containing 11.5 g./yd$^2$ of hydrophilic polyurethane), until the pores of the membrane were filled. The prepolymer in the membrane was moisture cured by exposing the filled membrane to moisture in the air for several days.

Irradiation

The coated membranes were irradiated with a cobalt 60 flux in a commercial sterilizing equipment. The samples were exposed to 2.5 M. rad and 5.0 M. rad doses.

Property Data

In the following Table, tensile strength and elongation are determined by ASTM Method D882.

TABLE I

TENSILE PROPERTIES OF UNIRRADIATED AND IRRADIATED COMPONENTS AND COMPOSITE COATINGS OF HPUR* AND EPTFE**

| Sample | | Irradiation Dose | | |
|---|---|---|---|---|
| | | 0 | 2.5 M rad | 5.0 M. rad |
| EPTFE | Tensile strength (psi) | 1160 | NM' | NM |
| | Elongation, % | 81 | NM | NM |
| HPUR | Tensile strength (psi) | 930 | 1853 | 1329 |
| | Elongation, % | 489 | 945 | 943 |
| EPTFE/HPUR coating | Tensile strength (psi) | 1315 | 422 (32%)$^4$ | 391 (30%) |
| | Elongation, % | 65 | 86 | 236 |
| EPTFE/HPUR +AO-1$^2$ coating | Tensile strength (psi) | 1480 | 829 (56%) | 772 (52%) |
| | Elongation, % | 106 | 550 | 584 |
| EPTFE/HPUR +AO-2$^3$ coating | Tensile strength (psi) | 1207 | 971 (80%) | 800 (66%) |
| | Elonagtion, % | 377 | 747 | 797 |

*HPUR = hydrophilic polyurethane resin
**EPTFE = expanded porous polytetrafluoroethylene
1. NM = not enough strength to measure
2. AO-1 = 1% Irganox 1010
3. AO-2 = 1% Irganox 1035
4. Numbers in ( ) represent % retained tensile strength

What is claimed is:

1. A composite comprising a polyurethane/expanded porous polytetrafluoroethylene in which a hindered phenol is present in the polyurethane portion.

2. A method of reducing sensitivity to ionizing radiation of polyurethane-expanded porous polytetrafluoroethylene composites which comprises adding a hindered phenol to the polyurethane portion.

3. The method of claim 2 wherein the polyurethane is hydrophilic and breathable.

* * * * *